(12) United States Patent
John et al.

(10) Patent No.: US 9,895,264 B2
(45) Date of Patent: Feb. 20, 2018

(54) GONIO LENS SYSTEM WITH STABILIZATION MECHANISM

(71) Applicant: Novartis AG, Basel (CH)

(72) Inventors: Steven John, Menlo Park, CA (US); Richard S. Lilly, Menlo Park, CA (US); Luke Clauson, Menlo Park, CA (US); Steven Vold, Menlo Park, CA (US); Brian Walsh, Menlo Park, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/987,133

(22) Filed: Jan. 4, 2016

(65) Prior Publication Data

US 2016/0193083 A1     Jul. 7, 2016

Related U.S. Application Data

(63) Continuation of application No. 14/507,123, filed on Oct. 6, 2014, now Pat. No. 9,226,658, which is a continuation of application No. 13/656,326, filed on Oct. 19, 2012, now Pat. No. 8,851,676.

(60) Provisional application No. 61/635,686, filed on Apr. 19, 2012, provisional application No. 61/550,337, filed on Oct. 21, 2011.

(51) Int. Cl.
| A61B 3/10 | (2006.01) |
| A61B 3/00 | (2006.01) |
| A61F 9/013 | (2006.01) |
| A61B 3/117 | (2006.01) |
| A61F 2/16 | (2006.01) |
| A61F 9/00 | (2006.01) |

(52) U.S. Cl.
CPC .............. *A61F 9/013* (2013.01); *A61B 3/117* (2013.01); *A61F 2/1662* (2013.01); *A61F 9/0017* (2013.01)

(58) Field of Classification Search
USPC .................................................. 351/200–246
See application file for complete search history.

(56) References Cited

U.S. PATENT DOCUMENTS

| 2,430,851 | A | | 11/1947 | Allen |
| 5,180,362 | A | | 1/1993 | Worst |
| 5,290,293 | A | | 3/1994 | Van Noy et al. |
| 5,537,164 | A | | 7/1996 | Smith |
| 6,976,758 | B2 | * | 12/2005 | Khaw ................... A61B 3/117 351/205 |
| 7,419,262 | B2 | * | 9/2008 | Whalen ................. A61B 3/125 351/159.67 |

(Continued)

OTHER PUBLICATIONS

PCT/US2016/052267, filed Sep. 16, 2016, WO 2017/051247.

(Continued)

*Primary Examiner* — Mohammed Hasan
(74) *Attorney, Agent, or Firm* — Mintz Levin Cohn Ferris Glovsky and Popeo, P.C.

(57) ABSTRACT

This disclosure relates generally to methods and devices for use in viewing and positioning an eye with a gonio lens system, such as during ocular exams and ocular surgeries. Some embodiments of the gonio lens system can include a gonio lens for viewing one or more tissues and structures of the eye. In addition, the gonio lens system can include one or more positioning features for controlling movement positioning of the eye.

7 Claims, 6 Drawing Sheets

(56) References Cited

U.S. PATENT DOCUMENTS

| | | | |
|---|---|---|---|
| 8,070,290 B2* | 12/2011 | Gille | A61B 3/117 351/159.02 |
| 8,851,676 B2 | 10/2014 | John et al. | |
| 9,226,658 B2* | 1/2016 | John | A61B 3/117 |
| 2004/0036839 A1 | 2/2004 | Fischer et al. | |
| 2004/0127843 A1* | 7/2004 | Tu | A61F 9/0017 604/27 |
| 2010/0118270 A1 | 5/2010 | Shea et al. | |
| 2010/0134759 A1* | 6/2010 | Silvestrini | A61B 3/117 351/206 |
| 2010/0274258 A1 | 10/2010 | Silvestrini et al. | |
| 2011/0213342 A1 | 9/2011 | Tripathi et al. | |

OTHER PUBLICATIONS

U.S. Appl. No. 13/865,927, filed Apr. 18, 2013, 2013-0281817.
U.S. Appl. No. 14/071,500, filed Nov. 4, 2013, 2014-0066831.
U.S. Appl. No. 14/078,206, filed Nov. 12, 2013, 2014-0135916.
U.S. Appl. No. 14/140,322, filed Dec. 24, 2013, 2014-0107556.
U.S. Appl. No. 14/163,364, filed Jan. 24, 2014, 2014-0213958.
U.S. Appl. No. 14/254,366, filed Apr. 16, 2014, 2014-0309599.
U.S. Appl. No. 14/260,041, filed Apr. 23, 2014, 2014-0323995.
U.S. Appl. No. 14/283,759, filed May 21, 2014, 2014-0364789.
U.S. Appl. No. 14/610,197, filed Jan. 30, 2015, 2015-0223982.
U.S. Appl. No. 14/706,893, filed May 7, 2015, 2015-0238360.
U.S. Appl. No. 15/005,745, filed Jan. 25, 2016, 2016-0135992.
U.S. Appl. No. 15/1655,759, filed May 26, 2016, 2016-0346125.
U.S. Appl. No. 15/268,305, filed Sep. 16, 2016, 2017-0079839.
U.S. Appl. No. 13/365,175, filed Feb. 2, 2012, 2012-0220917.
U.S. Appl. No. 13/865,947, filed Apr. 18, 2013, 2013-0281908.
U.S. Appl. No. 14/025,145, filed Sep. 12, 2013, 2014-0012279.
PCT/US2013/069617, filed Nov. 12, 2013, WO 2014/078288
U.S. Appl. No. 14/029,389, filed Sep. 17, 2013, 2014-0081195.
U.S. Appl. No. 14/199,737, filed Mar. 6, 2014, 2014-0188030.
U.S. Appl. No. 14/466,863, filed Aug. 22, 2014, 2014-0378886.
U.S. Appl. No. 14/804,008, filed Jul. 20, 2015, 2015-0320596.
U.S. Appl. No. 14/817,600, filed Aug. 4, 2015, 2015-0335487.

* cited by examiner

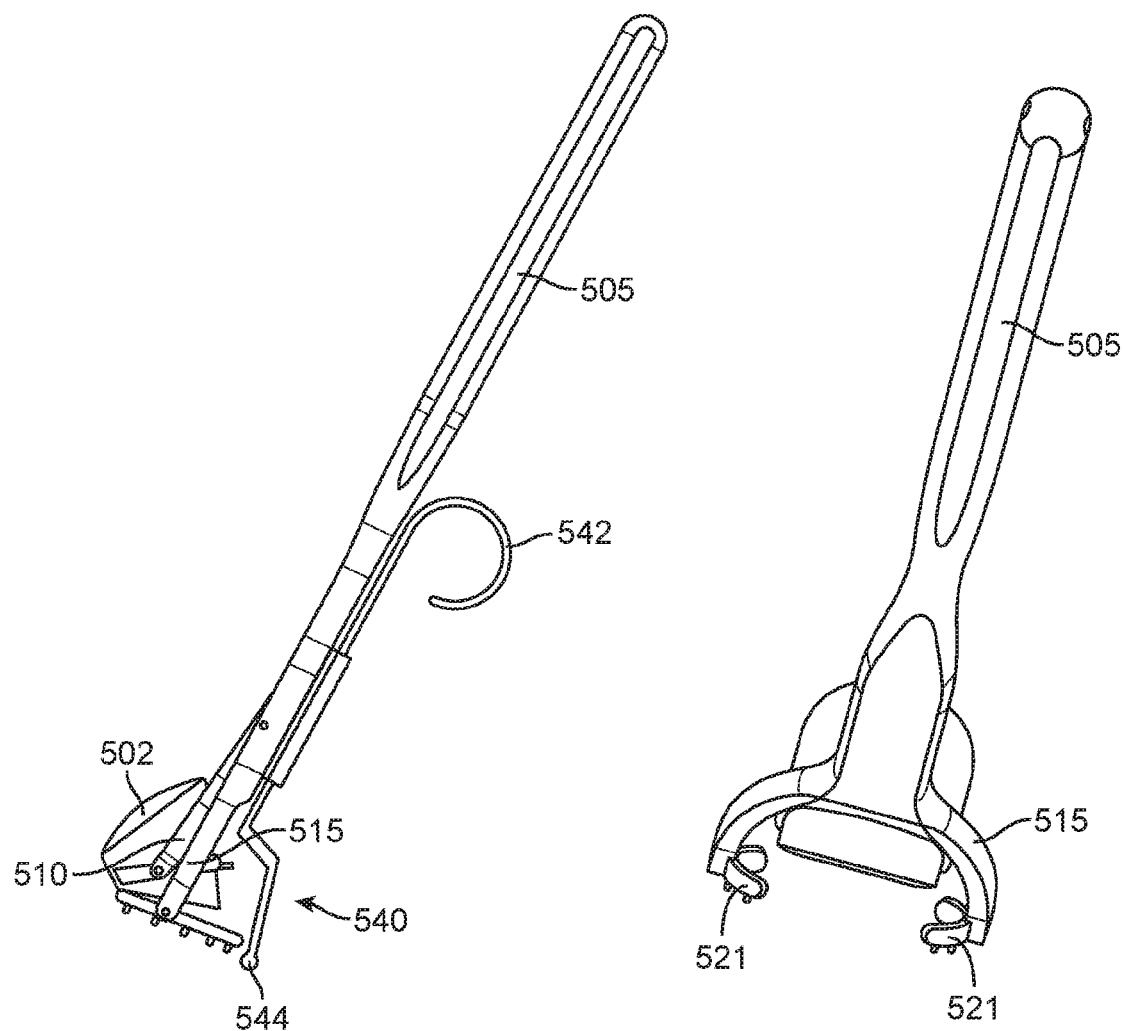

GONIO LENS SYSTEM WITH STABILIZATION MECHANISM

REFERENCE TO PRIORITY DOCUMENT

This application is a continuation of U.S. patent application Ser. No. 14/507,123, entitled "Gonio Lens System with Stabilization Mechanism" filed Oct. 6, 2014, issuing as U.S. Pat. No. 9,226,658 on Jan. 5, 2016, which in turn claims priority to U.S. patent application Ser. No. 13/656,326, titled "Gonio Lens System With Stabilization Mechanism," filed Oct. 19, 2012, now U.S. Pat. No. 8,851,676, which in turn claims priority of U.S. Provisional Patent Application Ser. No. 61/550,337, entitled "Gonio Lens System with Stabilization Mechanism," filed Oct. 21, 2011, and U.S. Provisional Patent Application Ser. No. 61/635,686, entitled "Gonio Lens System with Stabilization Mechanism," filed Apr. 19, 2012. Priority of the filing date of Oct. 21, 2011 is hereby claimed, and the disclosures of the aforementioned patent applications are hereby incorporated by reference each in its entirety.

BACKGROUND

This disclosure relates generally to methods and devices associated with a gonio lens system which includes a viewing lens and one or more features for controlling movement of the eye, such as during ocular surgeries.

Many ophthalmic surgical procedures utilize a gonio lens for visualization of the iridocorneal angle ("the angle") of the eye. The gonio lens can allow clinicians to visualize tissues comprising the angle of the eye which can be otherwise obstructed by the sclera. Visualization of the angle can be optimal when the clinician has control over the positioning and movement of the eye globe during surgery, which can be an issue due to one of many different types of anesthetics used to reduce pain (e.g., retro/peribulbar anesthesia, topical anesthesia, general anesthesia, etc.).

Movement of the eye globe during surgery (whether voluntary or involuntary) is a constant concern for the accuracy of implantation of a device, placement of surgical instruments, and for patient safety. Placement of ophthalmic implants in the eye, including the angle of the eye, can be critical to implant performance. At least some ophthalmic surgical procedures utilize either visualization or fixation techniques in order to allow for more precise handling and placement of implants. However, some visualization and fixation techniques can be cumbersome and apply an excessive amount of pressure on the eye which can complicate the procedure and damage the eye.

For example, added pressure on the eye can damage incisions in the eye, such as incisions formed during an ocular procedure. In addition, added pressure on the eye can cause deformation of the eye globe which can make the angle of the eye more difficult for a clinician to see. Particularly during ocular surgeries, such as implantation of an ocular implant in the angle of the eye, difficulties in viewing important eye tissue and structures can result in complications and extended procedure time.

In view of the foregoing, there is a need for an improved gonio lens system incorporating one or more features which can allow clinicians to visualize and have positioning control of the eye without the application of excessive pressure on the eye.

SUMMARY

Some embodiments disclosed herein include a gonio lens system including a handle, a gonio lens and a stabilization mechanism. The stabilization mechanism can be configured to couple the gonio lens to the handle. In addition, the stabilization mechanism can be further configured to allow the gonio lens to move relative to the handle.

Additionally, some embodiments disclosed herein include a gonio lens system comprising a handle, a gonio lens and an inner yoke. The inner yoke can be configured to couple the gonio lens to the handle. In addition, the inner yoke can be configured to permit the gonio lens to move relative to the handle.

Some methods of use of the gonio lens system disclosed herein can include using a gonio lens system for viewing a part of an eye. The method can include applying an ocular lubricant on a surface of the eye and placing a gonio lens of the gonio lens system in contact with the surface of the eye. In addition, the method can include engaging one or more positioning features which can be mechanically coupled to a handle of the gonio lens system with a part of the eye and moving the handle of the gonio lens system in order to at least one of stabilize the gonio lens system, move the eye, or change a viewing angle of the gonio lens. Additionally, the method can include viewing a part of the eye through the gonio lens.

Some methods of use of the gonio lens system disclosed herein can include using a gonio lens system for fixing an eye in a position during implantation of an ocular implant. The method can include applying an ocular lubricant on a surface of an eye and placing a gonio lens of the gonio lens system in contact with the surface of the eye. In addition, the method can include engaging one or more positioning features which are mechanically coupled to a handle of the gonio lens system with a part of the eye and moving the handle of the gonio lens system in order to position the eye in a position. Additionally, the method can include fixing the position of the eye with the handle and implanting an ocular implant in the eye.

Other features and advantages should be apparent from the following description of various embodiments, which illustrate, by way of example, the principles of the invention.

BRIEF DESCRIPTION OF THE DRAWINGS

These and other aspects will now be described in detail with reference to the following drawings.

FIG. 10 illustrates another embodiment of a gonio lens system including a scleral depressor feature.

FIG. 11 illustrates another embodiment of a gonio lens system including a pair of cleat arcs.

DETAILED DESCRIPTION

The disclosed gonio lens system incorporates both visualization and eye positioning features which can provide several advantages over current systems. Components of the disclosed system can be configured such that various movements of the visualization and eye positioning features are streamlined in order to achieve a more effective procedure. In addition, the streamlined movements of the visualization and positioning features can assist in minimizing pressure applied to the eye which can allow for improved visualization and protection of the eye.

Figure 1:
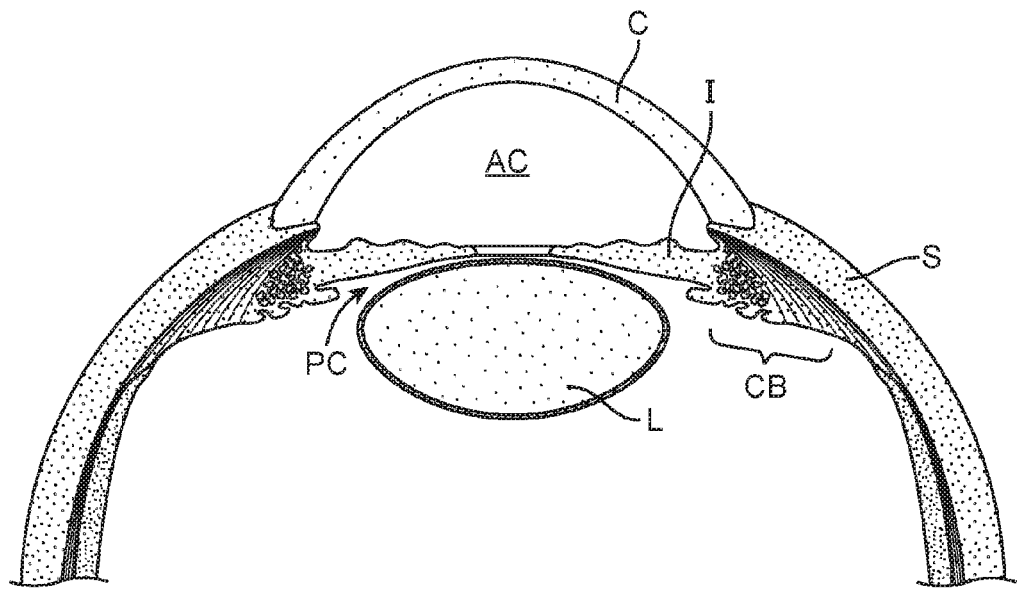
FIG. 1 shows a cross-sectional view of a portion of the human eye.

FIG. 1 shows a cross-sectional view of a portion of the human eye which is generally spherical and covered on the outside by the sclera S. The retina (not shown) lines the inside posterior half of the eye. The retina registers the light and sends signals to the brain via the optic nerve. The bulk of the eye is filled and supported by a vitreous body, which is a clear, jelly-like substance. The elastic lens L is located near the front of the eye. The lens L provides adjustment of focus and is suspended within a capsular bag from the ciliary body CB which contains the muscles that change the focal length of the lens L.

A volume in front of the lens L is divided into two by the iris I, which controls the aperture of the lens L and the amount of light striking the retina. The pupil is a hole in the center of the iris I through which light passes. The volume between the iris I and the lens L is the posterior chamber PC. The volume between the iris I and the cornea C is the anterior chamber AC. Both chambers are filled with a clear liquid known as aqueous humor. The ciliary body CB can continuously form aqueous humor in the posterior chamber PC by secretion from the blood vessels. The aqueous humor can flow around the lens L and iris I into the anterior chamber AC and exit the eye through the trabecular meshwork TM.

Figure 2:
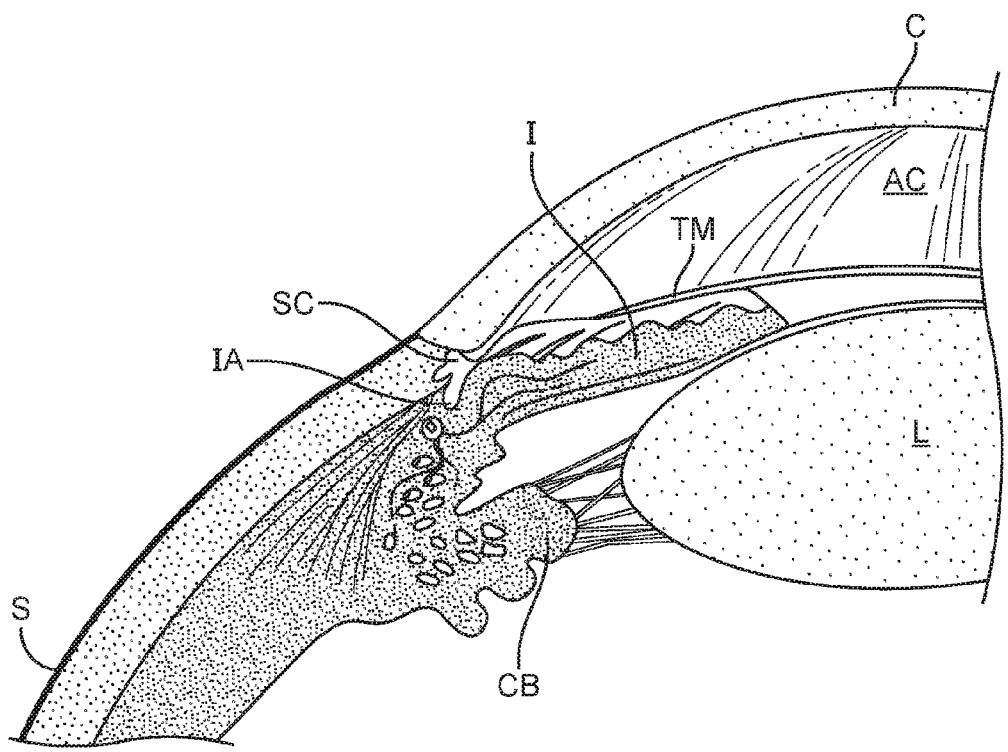
FIG. 2 is a cross-sectional view of a portion of the human eye showing the iridocorneal angle of the eye and surrounding tissue structures.

FIG. 2 is a cross-sectional view of a portion of the human eye showing the iridocorneal angle ("the angle") IA of the eye and surrounding tissue structures. A view of the angle IA can provide a variety of information to a clinician viewing the angle IA, including the health and condition of the eye. The angle IA is positioned between the iris I and the cornea C and plays an important role in the circulation of aqueous fluid in the eye.

The trabecular meshwork TM is an area of tissue in the eye located around the base of the cornea C, near the ciliary body CB, and is responsible for draining the aqueous humor from the eye via the anterior chamber AC. The trabecular meshwork TM is spongy and can allow fluid to drain into the Schlemm's canal SC. The Schlemm's canal SC, also known as canal of Schlemm or the scleral venous sinus, is a circular channel in the eye that collects aqueous humor from the anterior chamber AC and delivers it into the bloodstream via the anterior ciliary veins. The Schlemm's canal SC is essentially an endothelium-lined tube, resembling that of a lymphatic vessel. The inside of Schlemm's canal SC, nearest to the aqueous humor, is covered by the trabecular meshwork TM. This region can make the greatest contribution to outflow resistance of the aqueous humor.

The width of the iridocorneal angle IA is one factor affecting the drainage of aqueous humor from the eye's anterior chamber AC. A wide or open angle allows sufficient drainage of aqueous humor through the trabecular meshwork TM (unless obstructed), whereas a narrow angle can impede the drainage system and leave the patient susceptible to acute angle-closure glaucoma. Gonioscopy can indicate the angular width of the iridocorneal angle IA, such as by enabling a clinician to identify the number of ocular structures visible above the rim of the iris I. Generally the more structures visible, the wider the angle IA.

The disclosed gonio lens system can incorporate a gonio lens which can be used for angle visualization and one or more positioning features for control of the globe of the eye. The gonio lens system can be used in various procedures involving the eye, including ocular surgeries. The gonio lens and positioning features can be mounted onto a handle, each with their own stabilization mechanism. In addition, the gonio lens system can incorporate independent yet synergistic pivot and rotation points for the gonio lens and positioning features which can allow each to move with one or more degrees of freedom.

The gonio lens system can be used without exerting excessive pressure on the eye, such as on the anterior chamber. Added pressure on the eye during an ocular procedure can cause deformation of the eye globe which can make, for example, the angle of the eye more difficult for a clinician to see. Particularly during ocular surgeries, such as implantation of an ocular implant in the angle of the eye, difficulties in viewing important eye tissue and structures can result in complications and extended procedure time.

Visualization features of the gonio lens system can include a gonio lens which can be effective for viewing the angle of the eye. In addition, one or more stabilization features of the gonio lens system can assist in stabilizing the gonio lens on the eye. Additionally, some features can allow the gonio lens to move, such as slide along the cornea of the eye, independent of handle movement. Both stabilization and controlled movement of the gonio lens can be important features of the gonio lens system. For example, the ability of the clinician to move the gonio lens can allow a clinician to view a variety of tissues and structures of the eye, including the angle of the eye. By way of further example, the ability of the clinician to stabilize the gonio lens can assist in viewing the angle of the eye during implantation of an ocular implant. The stabilization and controlled movement of the gonio lens can assist in reducing procedure time and improve cost savings.

The one or more positioning features can provide both stabilization (e.g., fixing the eye in a specific position) and controlled movement (e.g., rotating) of the eye which can provide several advantages. By allowing the clinician to stabilize or fix the position of the eye globe with positioning features the clinician can efficiently and effectively view the eye and perform intricate ocular procedures, such as implantation of an ocular implant. In addition, positioning features can be used by the clinician to move the eye globe instead of changing viewing angles of microscopes during surgery which can be more time consuming. The ability of the positioning features to provide stabilization and controlled movement can also assist in reducing procedure costs and complications.

Figure 3:
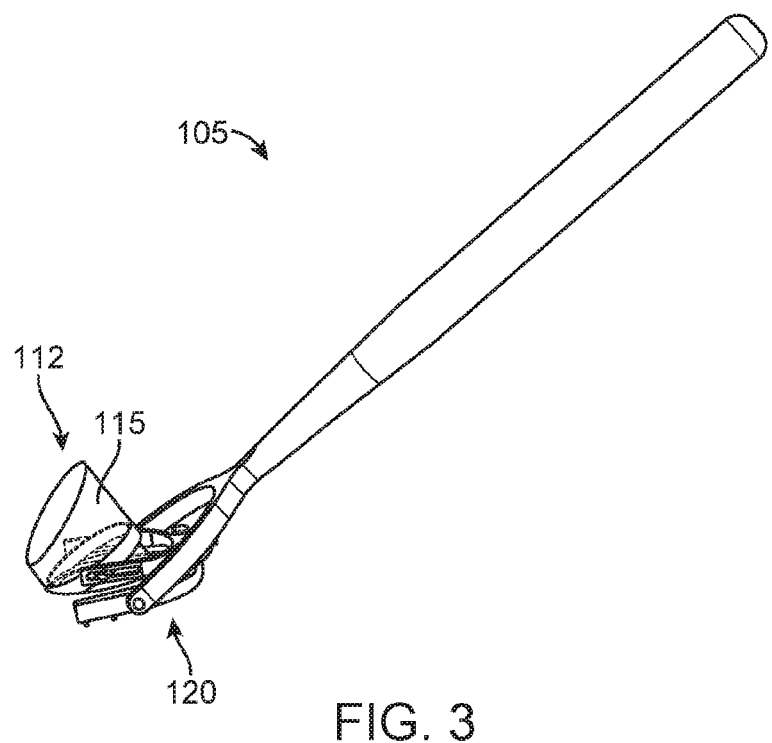
FIG. 3 shows a first embodiment of a gonio lens system having an elongated handle attached to a distal head region.

FIG. 3 shows a first embodiment of a gonio lens system 105 having an elongated handle 110 attached to a distal head region 112. The distal head region 112 can include a gonio lens 115 movably mounted to a stabilization mechanism 120. The stabilization mechanism 120 can be configured to be stabilized relative to a patient's eye while permitting movement of the gonio lens 115 relative to the handle 110. The gonio lens system 105 can be configured to be positioned adjacent a patient's eye using the handle 110 which can be grasped by a user, such as a clinician.

Figure 4:
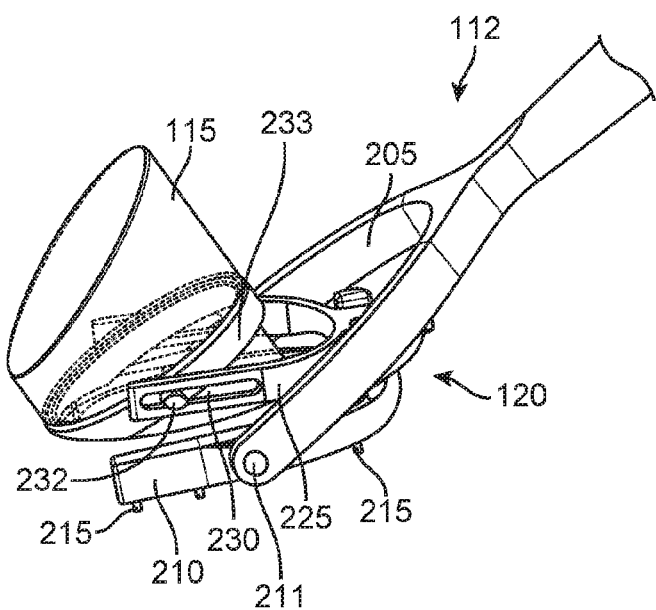
FIG. 4 shows a side perspective view of the distal head region of the gonio lens system of FIG. 3.
Figure 5:
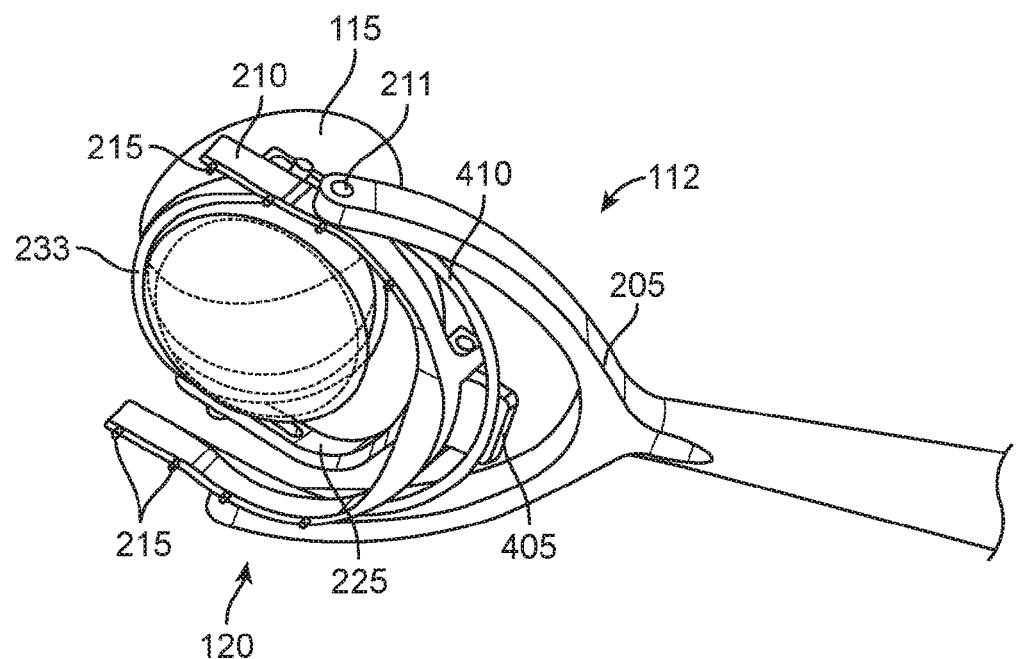
FIG. 5 shows a bottom perspective view of the distal head region of the gonio lens system of FIG. 3.
Figure 6:
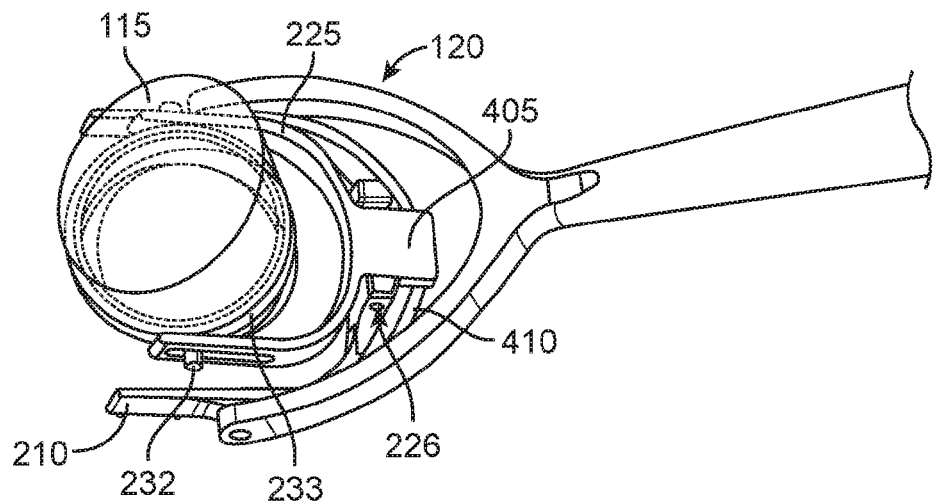
FIG. 6 shows a top perspective view of the distal head region of the gonio lens system of FIG. 3.

FIGS. 4-6 illustrate enlarged views of the distal head region 112 of the gonio lens system 105. As mentioned, the distal head region 112 can include a gonio lens 115 which can be movably mounted to a stabilization mechanism 120. The stabilization mechanism 120 can further assist in stabilizing one or more positioning features. As shown in FIGS. 4-6, the stabilization mechanism 120 can include a bracket 205 extending from a distal end of the handle 110 having extensions which can pivotally mount a stabilizing bracket 210. A bottom surface of the stabilizing bracket 210 can have one or more protrusions 215 which can be configured to interact with the eye, such as move and position the eye globe.

The protrusions 215 can be configured to be placed against the eye (e.g., sclera, conjunctiva) and can have a rounded shape in order to prevent damage to the eye during contact. The protrusions 215 can also include features, including surface features, which can assist the protrusions 215 in controlling the movement of the eye, such as either move or hold the eye in a position. In addition, any number of protrusions 215 having a variety of shapes and sizes can extend from the stabilizing bracket 210 for at least assisting with moving and positioning the eye.

The stabilizing bracket 210 can be pivotally mounted to the bracket 205 which can allow relative rotational movement between the bracket 205 and stabilizing bracket 210. A pair of pins 211 can assist in pivotally mounting the stabilizing bracket 210 to the bracket 205. The bracket 205 and stabilizing bracket 210 can be U-shaped, as shown in FIGS. 4-6, which can assist in allowing the bracket 205 and stabilizing bracket 210 to form a compact assembly and move relative to each other. Although the bracket 205 and stabilizing bracket 210 are shown as both being U-shaped, either the bracket 205 or stabilizing bracket 210 can be sized and shaped in a variety of sizes and shapes, as well as having similar or different shapes.

FIG. 4 shows an embodiment of a lens bracket 225 attached to a lens belt 233 with the lens belt 233 secured to the gonio lens 115. The lens belt 233 can be secured around at least a part of the gonio lens 115 and can include a pair of extruding pins 232. The pair of extruding pins 232 can slideably couple to a pair of slots 230 extending along a part of the lens bracket 225. The pair of slots 230 can allow the pair of extruding pins 232 to travel along the length of the slots 230, which can allow movement of the gonio lens 115 relative to at least the lens bracket 225. In this configuration, for example, the gonio lens 115 can slide along the cornea without moving the handle 110.

FIGS. 5 and 6 illustrate the lens bracket 225 which can be pivotally mounted to a support 226 of the stabilization bracket 210. The lens bracket 225 can be U-shaped, as shown in FIG. 6, or the lens bracket 225 can be any of a variety of shapes and sizes. In addition, the lens bracket 225 can include a tab 405 which can mate with or abut a biasing member 410. In this configuration, the biasing member 410 can limit the rotational movement of the lens bracket 225 and assist in biasing the lens bracket 225 and gonio lens 115 toward the user's eye when the gonio lens system 105 is in use. The biasing member 410 can be secured to a part of the stabilizing bracket 210 or any part of the stabilization mechanism 120 which can allow the biasing member 410 to assist in appropriately biasing the lens bracket 225.

The configuration of the various components of the stabilization mechanism 120, such as the stabilizing bracket 210, bracket 205 and lens bracket 225, can provide several degrees of freedom of movement of the gonio lens 115 relative to the handle 110. The degrees of movement can include rotational and translational movement, and the movement can be achieved while maintaining stabilization of the lens 115 relative to the eye. In addition, movement and stabilization of the components of the gonio lens system 105 can be done without applying excessive force to the eye.

In some embodiments of the gonio lens system 105, various components of the stabilization mechanism 120 can be immobilized relative to one another. For example, the position of the gonio lens 115 can be locked in position relative to the handle 110. In this regard, one or more actuators (not shown) may be included in the gonio lens system 105 which can be actuated, such as by a user, in order to lock and unlock one or more components relative to each other.

The gonio lens system 105 can be disposable or re-usable and components and materials used in re-usable gonio lens system 105 can be effectively cleaned, such as by autoclave. The handle 110 and stabilization mechanism 120 can be made out of one or more of a variety of materials including stainless steel, titanium, nitinol, plastics, or other equivalent materials. In addition, the handle 110 can include one or more malleable parts which can allow a clinician to customize the handle 110, such as for improved ergonomics.

The gonio lens 115 can be manufactured out of one or more of a variety of materials including optical glass, polymers, or other equivalent materials. In addition, the gonio lens 115 can be manufactured with one or more coating, such as coatings that can at least one of minimize reflection, increase lens strength, or minimize damage to the lens. In addition, the gonio lens 115 can be substituted with a variety of other ocular lenses. Additionally, the gonio lens 115 can be substituted with a gonio mirror.

In some methods of use of the gonio lens system 105 an ocular lubricant (such as a viscoelastic substance) can be placed on the surface of the cornea prior to placement of any part of the gonio lens system 105 against any part of the eye. Once the ocular lubricant has been applied, the gonio lens 115 can then be placed in contact with the cornea. In addition, the stabilization bracket 210 having one or more protrusions 215 can be placed on the conjunctiva above the sclera. The clinician can then use hand and wrist movements to manipulate the components of the gonio lens system 105. For example, the clinician can use the handle 110 to control the stabilization bracket 210, including the protrusions 215, to assist in either moving the eye or holding the eye in a desired position. In addition, the clinician can use auxiliary tools, including the clinician's hand, to move or lock one or more components of the gonio lens system 105. Additionally, the clinician can use an auxiliary tool or the clinician's hand to move the gonio lens 115 relative to the lens bracket 225 and handle 110 while securing the eye in position with the stabilization bracket 210.

Figure 7:
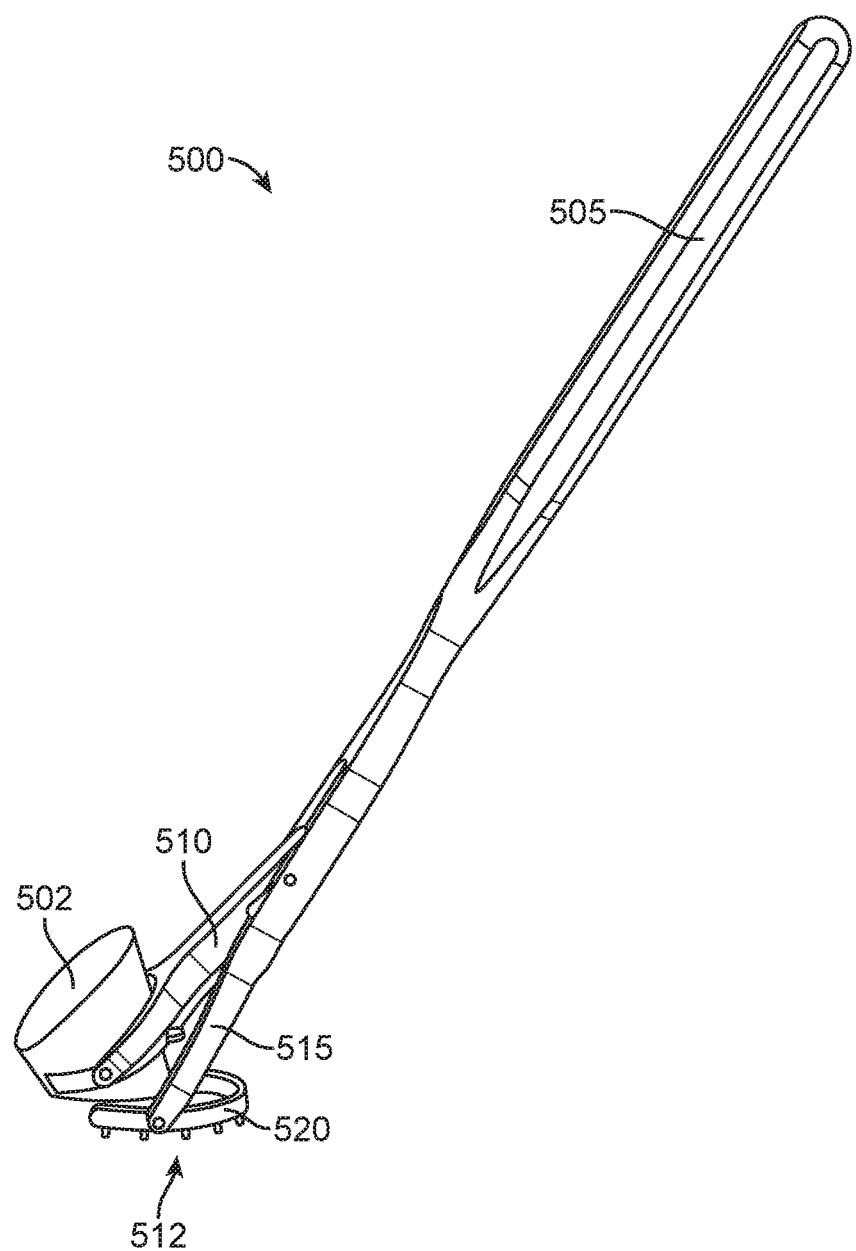
FIG. 7 illustrates another embodiment of a gonio lens system.
Figure 8:
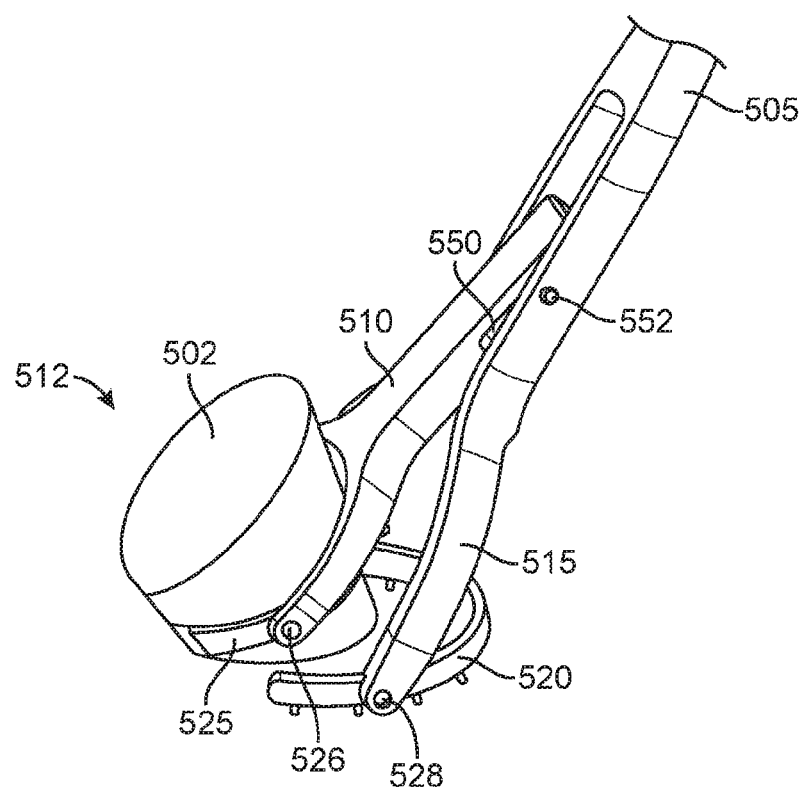
FIG. 8 shows a side perspective view of a distal head region of the gonio lens system of FIG. 7.
Figure 9:
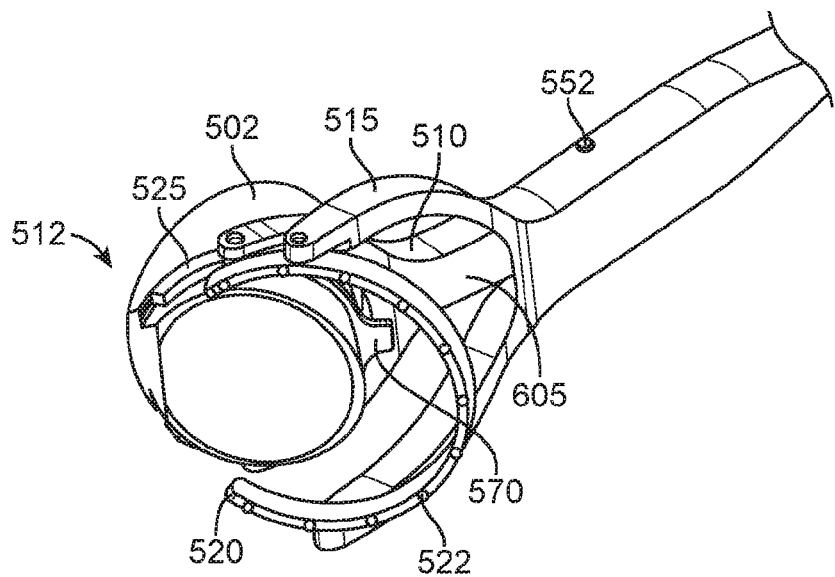
FIG. 9 shows a bottom perspective view of a distal head region of the gonio lens system of FIG. 7.

FIGS. 7-9 illustrate another embodiment of a gonio lens system 500. The gonio lens system 500 can include a handle 505 and a distal head region 512 positioned on a distal end of the handle 505. The distal head region 512 can include a gonio lens 502 which can assist a user in viewing various parts of the eye. In addition, the distal head region 512 can include one or more positioning features which can assist in moving and stabilizing a position of the eye.

FIGS. 8 and 9 show enlarged views of the distal head region 512, which can include an inner yoke 510 and an outer yoke 515. The gonio lens 502 can be pivotally mounted to the inner yoke 510 via a pair of pins 526 extending from a lens belt 525. As shown in FIGS. 8 and 9, the lens belt 525 can secure and extend around at least a part of the gonio lens 502. The inner yoke 510 can be pivotally mounted to either a part of the handle 505 or the outer yoke 515 such that the inner yoke 510 can pivot relative to the outer yoke 515 and handle 505.

The gonio lens system 500 can also include a cleat ring 520 having one or more protrusions or cleats 522 which can assist in positioning the eye. The cleat ring 520 can be U-shaped and pivotally mounted to the outer yoke 515, such as via a pair of pins 528 extending from a part of the cleat ring 520. The outer yoke 515 can include one or more hard stop features 530 which can assist in limiting the rotational motion of the cleat ring 520 relative to the outer yoke 515. In some implementations, the cleat ring 520 can be rigidly connected to the outer yoke 515 which can prevent movement of the cleat ring 520 relative to the handle 505 while still allowing the gonio lens 502 to move freely relative to both the handle 505 and cleat ring 520.

As shown in FIGS. 8 and 9, the outer yoke 515 can extend distally from the distal end of the handle 505. An axis 552 located adjacent the distal end of the handle 505 can couple with, such as extend through, a slot 550 extending along a length of the inner yoke 510. The axis 552 can assist in movably coupling the inner yoke 510 to both the handle 505 and outer yoke 515. For example, coupling of the axis 552 to the slot 550 can allow the inner yoke 510 to rotate and translate relative to at least the outer yoke 515 and handle 505.

Features of the inner yoke 510 and handle 505 can provide hard stops for both the rotation and translation motion of the inner yoke 510 relative to the handle 505. The inner yoke 510 can include a hard stop 605 which can assist in limiting the rotation of the gonio lens 502. For example, the lens belt 525 can include a tab 570 which can abut or mate with the hard stop 605 and limit the rotation of the gonio lens 502 relative to the inner yoke 510. The rotational and translational aspects of the various components allow the gonio lens system 500 to conform to the shape of the eye globe and minimize pressure applied on the eye.

Additional components can be incorporated into the gonio lens system 500 in order to provide additional movement of either the gonio lens 502 or cleat ring 520. Alternatively, fewer components can be incorporated in the gonio lens system 500, such as in order to restrict the available movements of either the gonio lens 502 or cleat ring 520. The availability of motions of either the gonio lens 502 or cleat ring 520 can be based on a user's preference or the application for which the gonio lens system 500 is to be used for.

Various configurations of the gonio lens system have been contemplated, including gonio lens systems which do not include a handle 505. In this configuration, the clinician can interact with and adjust the distal head region 512 without the use of the handle 505. Alternatively or in addition, the gonio lens system can include a handle adapter which can allow the gonio lens system to be used with or without a handle 505. The handle adapter can include one or more adaptable features, such as threaded holes, for allowing the handle 505 to couple to the handle adapter. In addition, more than one adaptable feature can allow the handle 505 to couple to the handle adapter in more than one way in order to form more than one configuration of the gonio lens system.

For example, the handle adapter can include three adaptable features, such as threaded holes, in three different positions which can allow the handle 505 to form three different configurations, such as different angular configurations between the gonio lens 502 and handle 505. The different angular configurations of the gonio lens 502 relative to the handle 505 can provide a variety of viewing angles and ease of manipulation of the gonio lens 502 depending on, for example, whether the user is left handed or right handed. In addition, the various adaptable features can be useful for configuring the gonio lens system to better accompany a variety of procedures.

In some implementations, the cleat ring 520 can include various features, including a variety of cleat patterns. The cleat ring 520 can also have any number of configurations, including a configuration where the cleat ring 520 is comprised of more than one cleat arc 521, as shown in FIG. 11. In addition, the cleat ring 520 and cleat arcs 521 can vary in shape and diameter in order to accommodate varying corneal diameters.

In some implementations, the cleat ring 520 or cleat arcs 521 can have one or more cut-out portions which can assist in preventing pressure or force from being applied to specific locations of the eye. In addition, the cut-outs can prevent obstruction to specific locations of the eye. Therefore, cut-out portions can assist in the implantation of various implants or surgical techniques requiring either access or less pressure applied to specific locations of the eye.

Alternatively or in addition, some implementations of the gonio lens system 500 can have one or more alternate fixation features, such as vacuum or suture anchoring features. For example, a stabilization feature, such as the cleat ring 520 or cleat arcs 521, can include a series of vacuum inlets which can suck the globe firmly against the stabilization feature. By way of further example, a stabilization feature, such as the cleat ring 520 or cleat arcs 521, can include a suture anchoring feature which can suture a part of the eye to the stabilization feature. Any number of a variety of anchoring features can be included in any gonio lens system 500 for either securing or manipulating the eye without departing from the scope of this disclosure.

A variety of additional features can be either included or adaptable to the gonio lens system 500. FIG. 10 illustrates an embodiment of the gonio lens system 500 including a scleral depressor 540 feature. The scleral depressor 540 can be permanently or removeably coupled to a part of the gonio lens system 500, such as the handle 505. In addition, the scleral depressor 540 can include a finger adapter 542 for allowing a user's finger to control the scleral depressor 540. Alternatively or in addition, some implementations of the finger adapter 542 can be configured to move the gonio lens 502, such as in the proximal or distal direction relative to the handle 505. This can allow the user to easily control the position of the gonio lens 502, such as raise or lower the gonio lens 502 onto the eye with the use of one or more fingers of the hand grasping the handle 505.

In some implementations, the scleral depressor 540 can be slidingly coupled to the handle 505 such that a user can push or pull the finger adapter 542 in order to cause the scleral depressor 540 to extend distally or proximally, respectively, relative to the handle 505. As shown in FIG. 10, a distal end 544 of the scleral depressor 540 can extend distally past the cleat ring 520 which can allow the scleral depressor 540 to apply a force on the sclera while the cleat ring 520 is positioned on the eye. The scleral depressor 540 can also be retracted so that the distal end 544 of the scleral depressor 540 does not extend distally past the cleat ring 520. The distal end 544 of the scleral depressor 540 can be sized and shaped (e.g., a rounded configuration) in order to prevent damage upon contact and applying a force to the eye.

The scleral depressor 540 can be used to bring eye tissues and structures (e.g., the iridocorneal angle) into a field of view, such as through the gonio lens 502. For example, improved visualization of the angle can be achieved with a force applied on the eye by the scleral depressor 540 causing the angle structures to be brought more forward and into the anterior chamber. Therefore, the scleral depressor 540 can improve visualization by bringing the angle structures more forward into the anterior chamber and thereby reducing the required depth of visualization. The scleral depressor 540 can also be useful for accessing and visualizing Schlemm's canal, such as for implanting an ocular implant in the suprachoroidal/supraciliary space, or any equivalent or related action.

In some methods of use of the gonio lens system 500 an ocular lubricant (such as a viscoelastic substance) can be placed on the surface of the cornea prior to placement of any part of the gonio lens system 500 against any part of the eye. Once the ocular lubricant has been applied, the gonio lens 502 can then be placed in contact with the cornea. In addition, the cleat ring 520 or cleat arcs 521 having one or more protrusions 522 can be placed on the eye, such as on the conjunctiva above the sclera. The clinician can use hand and wrist movements to manipulate the components of the gonio lens system 500. For example, the clinician can use the handle 505 to control the cleat ring 520 or cleat arcs 521, including the protrusions 522, to assist in either moving the eye or stabilizing the eye in a desired position. As mentioned above, fixing or stabilizing the eye in a desired position can be beneficial in some procedures, such as during implantation of an ocular implant. In addition, the clinician can use auxiliary tools, including the clinician's hand, to move or lock one or more components of the gonio lens system 500. Additionally, the clinician can use an auxiliary tool or the clinician's hand to move the gonio lens 502 relative to the handle 505 while securing the eye in position with the cleat ring 520 or cleat arcs 521.

In some methods of use of the gonio lens system 500, the clinician can engage the finger adapter 542 of the scleral depressor 540 in order to cause the scleral depressor 540 to extend distally or proximally relative to the handle 505. For example, the clinician can push the finger adapter 542 in order to distally extend the scleral depressor 540 and cause the distal end 544 to apply a force onto the eye, such as on the sclera. This can allow the clinician to improve visualization of tissues and structures of the eye, including the angle of the eye. While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A gonio lens system, comprising:
    a handle having a forked end that defines two prongs;
    a stabilization bracket having one or more protrusions for positioning on the eye, wherein the stabilization bracket is formed of a U-shaped body that is rotatably attached to the forked end of the handle inside the two prongs;
    a U-shaped lens bracket attached to the stabilization bracket;
    a gonio lens movably attached to the lens bracket.

2. The system in claim 1, wherein the protrusions include at least one of a rounded shape and a surface feature for controlling movement of the eye.

3. The system in claim 1, further comprising a lens belt secured to at least a part of the gonio lens, with the lens belt including a pair of extruding pins coupled to a pair of slots extending along a part of the lens bracket.

4. The system in claim 3, wherein the lens bracket is pivotally mounted to the stabilization bracket.

5. The system in claim 1, wherein at least one of the handle or stabilization mechanism is made out of one or more materials, including stainless steel, titanium, nitinol, plastics, or other equivalent materials.

6. The system in claim 1, wherein the gonio lens is manufactured out of one or more materials including optical glass, polymers, or other equivalent materials.

7. The system in claim 1, wherein the gonio lens is coated with one or more coatings, including coatings which at least one of minimize reflection, increase lens strength, and minimize damage to the lens.

* * * * *